US012780788B2

(12) United States Patent
Wang et al.

(10) Patent No.: US 12,780,788 B2
(45) Date of Patent: Nov. 3, 2026

(54) METHOD FOR PREPARING AZOXYSTROBIN AND INTERMEDIATE THEREOF

(71) Applicant: ANHUI GUANGXIN AGROCHEMICAL CO., LTD., Xuancheng (CN)

(72) Inventors: Zhenyu Wang, Xuancheng (CN); Haihui Li, Xuancheng (CN); Liang Chen, Xuancheng (CN); Xiaoguo Zhang, Xuancheng (CN); Jianyong Miao, Xuancheng (CN); Xiaoqin Zhang, Xuancheng (CN)

(73) Assignee: ANHUI GUANGXIN AGROCHEMICAL CO., LTD., Xuancheng (CN)

( * ) Notice: Subject to any disclaimer, the term of this patent is extended or adjusted under 35 U.S.C. 154(b) by 521 days.

(21) Appl. No.: 18/270,905

(22) PCT Filed: Jan. 16, 2023

(86) PCT No.: PCT/CN2023/072327

§ 371 (c)(1),
(2) Date: Jul. 5, 2023

(87) PCT Pub. No.: WO2023/226456

PCT Pub. Date: Nov. 30, 2023

(65) Prior Publication Data

US 2024/0383864 A1 Nov. 21, 2024

(30) Foreign Application Priority Data

May 26, 2022 (CN) ......................... 202210578038.1

(51) Int. Cl.
*C07D 239/52* (2006.01)
*B01J 31/02* (2006.01)

(52) U.S. Cl.
CPC ........ *C07D 239/52* (2013.01); *B01J 31/0244* (2013.01)

(58) Field of Classification Search
None
See application file for complete search history.

(56) References Cited

U.S. PATENT DOCUMENTS

| | | | | |
|---|---|---|---|---|
| 9,234,109 | B2 * | 1/2016 | Turek | C09D 11/38 |
| 2008/0214587 | A1 | 9/2008 | Whitton et al. | |
| 2010/0063275 | A1 | 3/2010 | Beveridge et al. | |
| 2016/0090365 | A1 | 3/2016 | Wang et al. | |
| 2016/0137612 | A1 | 5/2016 | Lindsay | |
| 2016/0200687 | A1 | 7/2016 | Chen et al. | |
| 2022/0185784 | A1 | 6/2022 | Kini et al. | |
| 2022/0194903 | A1 | 6/2022 | Kini et al. | |

FOREIGN PATENT DOCUMENTS

| | | | | |
|---|---|---|---|---|
| CN | 101163682 | A | | 4/2008 |
| CN | 101522642 | A | | 9/2009 |
| CN | 102311392 | A | | 1/2012 |
| CN | 103265496 | A | | 8/2013 |
| CN | 103467387 | A | | 12/2013 |
| CN | 104926736 | A | | 9/2015 |
| CN | 105246878 | A | | 1/2016 |
| CN | 109529928 | A | | 3/2019 |
| CN | 113767093 | A | | 12/2021 |
| CN | 113825744 | A | | 12/2021 |
| CN | 114195723 | | * | 3/2022 |
| CN | 114195723 | A | | 3/2022 |
| CN | 114957134 | A | | 8/2022 |
| GB | 2291874 | B | | 9/1996 |
| WO | 9208703 | A1 | | 5/1992 |
| WO | 2006114572 | A2 | | 11/2006 |
| WO | WO2008/043978 | A1 | * | 4/2008 |
| WO | 2017060917 | A1 | | 4/2017 |
| WO | 2020212919 | A1 | | 10/2020 |
| WO | 2020212928 | A1 | | 10/2020 |
| WO | WO2020/212919 | | * | 10/2020 |

OTHER PUBLICATIONS

Turner (Inorg. Chem. 2013, 52, 7344-7351).*
Zhang (Dalton Trans., 2017, 46, 899).*
Schareina (Organic Process Research & Development 2008, 12, 537-539).*
Zhong (Synthetic Communications 2004, 34:23, 4301-4311).*
The 1st Office Action dated Aug. 30, 2023 for the Chinese Patent Application No. CN202210578038.1.
The European search report issued on Jan. 8, 2025 for EP23729649.6.
International Search Report for PCT/CN2023/072327 mailed May 9, 2023, ISA/CN.
Fan Zhao-hui et.al Efficient Catalyst for the Synthesis of Azoxystrobin and Its Intermediate, Agrochemicals, vol. 58, No. 7 Jul. 2019.

* cited by examiner

*Primary Examiner* — Valerie Rodriguez-Garcia
(74) *Attorney, Agent, or Firm* — Yue (Robert) Xu; Apex Attorneys at Law, LLP

(57) ABSTRACT

The present disclosure relates to a method for preparing azoxystrobin. This method uses a pentacyclic azole-based compound or a salt thereof, preferably 1-methylimidazole or pentetrazol, as a catalyst to prepare azoxystrobin, which can greatly reduce dimer impurities, improving the purity of the product. Moreover, the catalyst is cheap and easy to be synthesized, and can significantly reduce production costs, thus having good industrial application value.

10 Claims, No Drawings

METHOD FOR PREPARING AZOXYSTROBIN AND INTERMEDIATE THEREOF

CROSS REFERENCE TO RELATED APPLICATIONS

This application is the U.S. national phase of International Application No. PCT/CN2023/072327 field on Jan. 16, 2023, which claims the priority of Chinese Patent Application No. 202210578038.1, filed with the China National Intellectual Property Administration on May 26, 2022, and titled with "METHOD FOR PREPARING AZOXYSTROBIN AND INTERMEDIATE THEREOF", which is hereby incorporated by reference in its entirety.

FIELD

The present disclosure relates to a method for preparing azoxystrobin and an intermediate thereof.

BACKGROUND

Azoxystrobin is a novel high-efficiency, broad-spectrum and systemic methoxyacrylate fungicide, having a chemical name of methyl (E)-2-[2-[6-(2-cyanophenoxy) pyrimidin-4-yloxy]phenyl]-3-methoxyacrylate. Such fungicide can be used for spraying on stems or leaves, treating seeds or soil, and has good activity against almost all fungal diseases. Owing to its characteristics of high efficiency, broad spectrum and low toxicity, azoxystrobin has become a hot spot in the recent development, and can be synthesized by a variety of synthetic routes as reported.

WO92/08703 discloses a method for preparing azoxystrobin through a reaction of 2-cyanophenol with methyl (E)-2-[2-(6-chloro-pyrimidin-4-yloxy)phenyl]-3-methoxyacrylate. This method is the synthetic method adopted by most production enterprises at present, involving synthesizing the key intermediate methyl (E)-2-[2-(6-chloro-pyrimidin-4-yloxy)phenyl]-3-methoxyacrylate under harsh synthetic conditions such as high temperature and high vacuum which makes the synthesis difficult, leading to a large difference from the reported reaction yield.

WO2006/114572 and WO2008/043978 disclose that use of DABCO as a catalyst to prepare azoxystrobin or a new azoxystrobin acetal precursor will significantly reduce the usage of the relatively expensive catalyst but does not reduce the yield. This method reduces not only production costs, but also the amount of catalysts discharged in wastewater.

WO2017/060917 discloses a method for preparing azoxystrobin by reacting o-cyanophenol with methyl 3-methoxy (2-(2-(6-chloropyrimidin)-4-yl)oxyphenyl) acrylate in the presence of a catalyst selected from the group consisting of crown ethers and polyethylene glycol (PEG).

WO2020/212919 discloses a method for preparing azoxystrobin and its intermediate by using diazabicycloundec-7-ene and diazabicyclnon-5-ene as catalysts, which can reduce dimer impurities.

Fan Zhaohui et al. (An efficient catalyst for preparing azoxystrobin and its intermediate [J]. Pesticides, 2019, 58(7):483-486) disclose a method for preparing azoxystrobin by using 1-azabicyclo[3.2.1]octan-6-ol as a catalyst. This method yields a product that is a mixture of methyl 2-(2-((6-chloropyrimidin-4-yl)oxy)phenyl)-3,3-dimethoxyacrylate and methyl E-2-{2-[6-chloropyrimidin-4-yloxy]phenyl}-3-methoxyacrylate, at a total content of 95.4%.

The conventional methods for preparing azoxystrobin and its intermediate cannot meet the requirement of industrial production in respect of yield and purity. Therefore, it is desired to provide an efficient method for preparing azoxystrobin and its intermediate.

The inventors of this application surprisingly found that the method, according to this disclosure, for preparing azoxystrobin and its intermediate by using a pentacyclic azole-based compound as a catalyst, can provide the desired compound with high yield and high purity substantially free of impurities.

SUMMARY

In the first aspect, the present disclosure provides a method for preparing azoxystrobin and an intermediate thereof.

In another aspect, the present disclosure provides use of a pentacyclic azole-based compound or a salt thereof as a catalyst for preparing azoxystrobin represented by formula I;

I

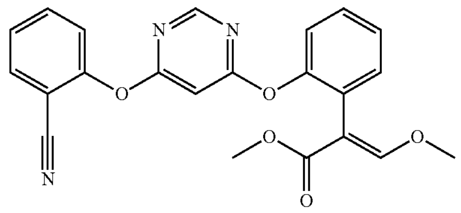

the pentacyclic azole-based compound has a structure selected from the group consisting of:

Formula 1

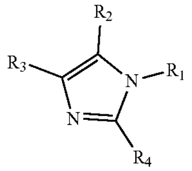

Formula 2

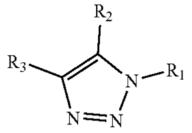

Formula 3

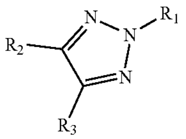

Formula 4

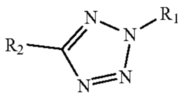

Formula 5

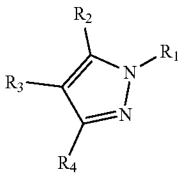

-continued

Formula 6

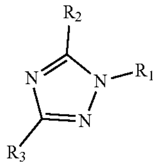

Formula 7

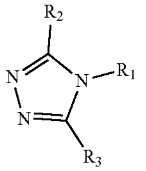

Formula 8

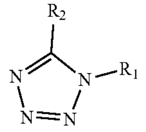

and

Formula 9

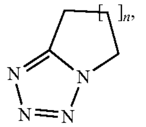

wherein:

R1 is selected from the group consisting of C1-C10 straight-chain alkyl, C1-C10 branched-chain alkyl, cyano, amino and C1-C10 alkylamino;

R2-, R3 and R4 are each independently selected from the group consisting of hydrogen, C1-C10 straight-chain alkyl, C1-C10 branched-chain alkyl, cyano, amino, C1-C10 alkylamino, hydroxyl, halogen and nitro;

n is an integer selected from the group consisting of 1, 2 and 3;

preferably, R1 is selected from the group consisting of C1-C6 straight-chain alkyl and C1-C6 branched-chain alkyl; more preferably, R1 is selected from the group consisting of methyl, ethyl, n-propyl, n-butyl, n-pentyl, isopropyl, isobutyl and isopentyl;

preferably, R2-, R3 and R4 are each independently selected from the group consisting of hydrogen, C1-C6 straight-chain alkyl and C1-C6 branched-chain alkyl; more preferably, R2-, R3 and R4 are each independently selected from the group consisting of hydrogen, methyl, ethyl, n-propyl, n-butyl, n-pentyl, isopropyl, isobutyl and isopentyl;

preferably, n is 2 or 3; more preferably, n is 3.

preferably, the pentacyclic azole-based compound is represented by formula 1 or formula 9:

Formula 1

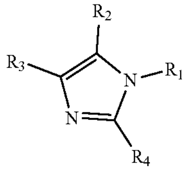

-continued

Formula 9

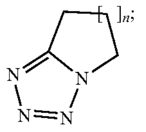

wherein R1-, R2-, R3-, R4 and n are defined as above;

more preferably, the pentacyclic azole-based compound is 1-methylimidazole or pentetrazol.

In another aspect, the present disclosure provides use of a pentacyclic azole-based compound or a salt thereof as a catalyst for preparing a compound represented by formula III or formula VI;

Compound III

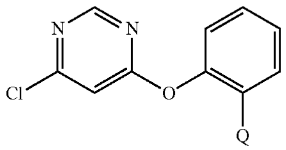

Compound IV

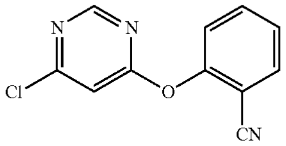

wherein Q is selected from the group consisting of a methyl (E)-2-(3-methoxy)acrylate group, a methyl 2-(3,3-dimethoxy)propionate group, and a combination thereof;

the pentacyclic azole-based compound has a structure selected from the group consisting of:

Formula 1

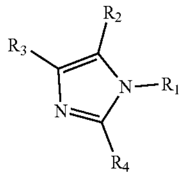

Formula 2

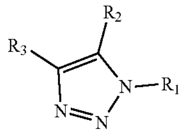

Formula 3

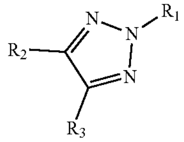

Formula 4

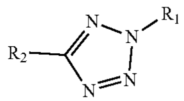

-continued

Formula 5

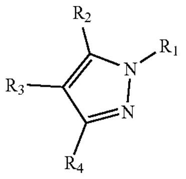

Formula 6

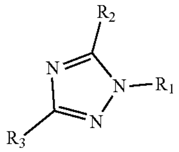

Formula 7

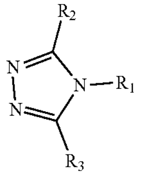

Formula 8

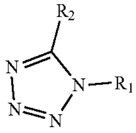

and

Formula 9

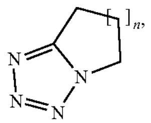

wherein: R1 is selected from the group consisting of C1-C10 straight-chain alkyl, C1-C10 branched-chain alkyl, cyano, amino and C1-C10 alkylamino;

R2-, R3 and R4 are each independently selected from the group consisting of hydrogen, C1-C10 straight-chain alkyl, C1-C10 branched-chain alkyl, cyano, amino, C1-C10 alkylamino, hydroxyl, halogen and nitro;

n is an integer selected from the group consisting of 1, 2 and 3;

preferably, R1 is selected from the group consisting of C1-C6 straight-chain alkyl and C1-C6 branched-chain alkyl; more preferably, R1 is selected from the group consisting of methyl, ethyl, n-propyl, n-butyl, n-pentyl, isopropyl, isobutyl and isopentyl;

preferably, R2-, R3 and R4 are each independently selected from the group consisting of hydrogen, C1-C6 straight-chain alkyl and C1-C6 branched-chain alkyl; more preferably, R2-, R3 and R4 are each independently selected from the group consisting of hydrogen, methyl, ethyl, n-propyl, n-butyl, n-pentyl, isopropyl, isobutyl and isopentyl;

preferably, n is 2 or 3; more preferably, n is 3;

preferably, the pentacyclic azole-based compound is represented by formula 1 or formula 9:

Formula 1

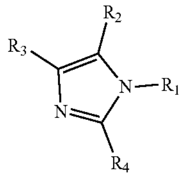

Formula 9

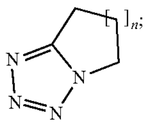

wherein: R1-, R2-, R3-, R4 and n are defined as above;

more preferably, the pentacyclic azole-based compound is 1-methylimidazole or pentetrazol.

In another aspect, the present disclosure provides a method for preparing azoxystrobin represented by formula I:

I

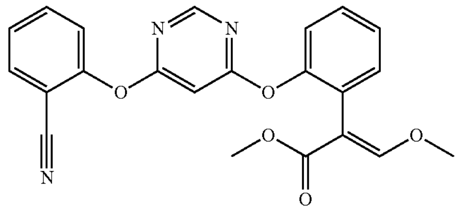

wherein the method comprises:

step 1), reacting a compound represented by formula II with a compound represented by formula III in the presence of a pentacyclic azole-based compound or a salt thereof, as a catalyst, to prepare the azoxystrobin represented by formula I,

II

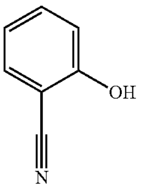

III

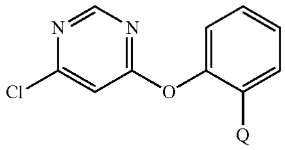

wherein Q is selected from the group consisting of a methyl (E)-2-(3-methoxy)acrylate group, a methyl 2-(3,3-dimethoxy)propionate group, and a combination thereof;

the pentacyclic azole-based compound has a structure selected from the group consisting of:

Formula 1

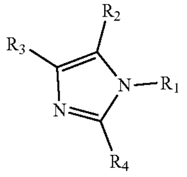

Formula 2

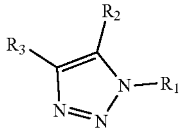

Formula 3

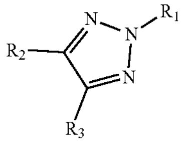

Formula 4

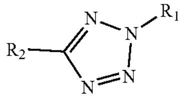

Formula 5

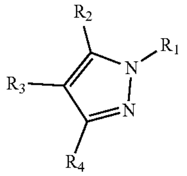

Formula 6

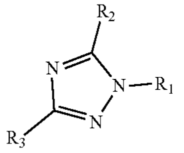

Formula 7

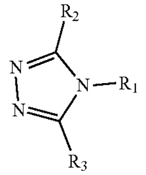

Formula 8

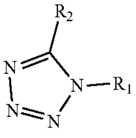

and

Formula 9

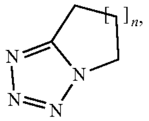

wherein

R1 is selected from the group consisting of C1-C10 straight-chain alkyl, C1-C10 branched-chain alkyl, cyano, amino and C1-C10 alkylamino;

R2-, R3 and R4 are each independently selected from the group consisting of hydrogen, C1-C10 straight-chain alkyl, C1-C10 branched-chain alkyl, cyano, amino, C1-C10 alkylamino, hydroxyl, halogen and nitro;

n is an integer selected from the group consisting of 1, 2 and 3;

preferably, R1 is selected from the group consisting of C1-C6 straight-chain alkyl and C1-C6 branched-chain alkyl; more preferably, R1 is selected from the group consisting of methyl, ethyl, n-propyl, n-butyl, n-pentyl, isopropyl, isobutyl and isopentyl;

preferably, R2-, R3 and R4 are each independently selected from the group consisting of hydrogen, C1-C6 straight-chain alkyl and C1-C6 branched-chain alkyl; more preferably, R2-, R3 and R4 are each independently selected from the group consisting of hydrogen, methyl, ethyl, n-propyl, n-butyl, n-pentyl, isopropyl, isobutyl and isopentyl;

preferably, n is 2 or 3; more preferably, n is 3;

preferably, the pentacyclic azole-based compound is represented by formula 1 or formula 9:

Formula 1

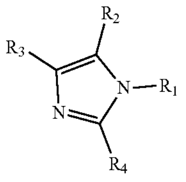

Formula 9

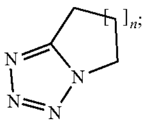

most preferably, the pentacyclic azole-based compound is 1-methylimidazole or pentetrazol.

In the method for preparing the compound represented by formula I, the compound represented by formula III is a compound represented by formula IIIa or formula IIIb:

Compound IIIa

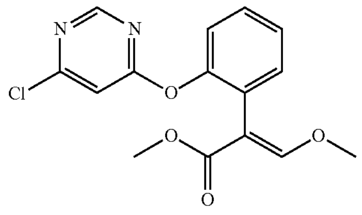

Compound IIIb

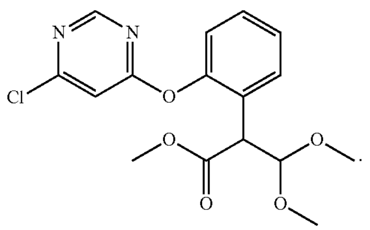

In the method for preparing the compound represented by formula I, the compound represented by formula III is a mixture of compound IIIa and compound IIIb:

Compound IIIa

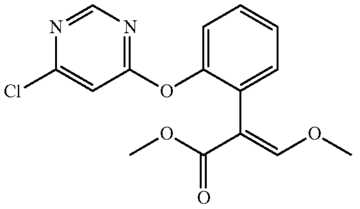

Compound IIIb

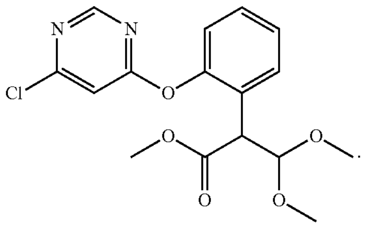

In another aspect, the aforementioned method for preparing the compound represented by formula I further comprises:

step 2), reacting compound IV with compound V under the catalysis by the pentacyclic azole-based compound or the salt thereof, as a catalyst, to prepare the compound represented by formula III:

Compound IV

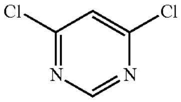

Compound V

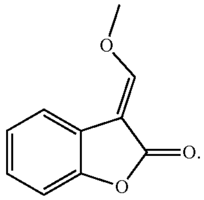

Preferably, the pentacyclic azole-based compound or the salt thereof in step 1) is used in an amount from 0.01 mol % to 10 mol %, preferably 0.05 mol % to 5 mol % of the compound represented by formula III; the pentacyclic azole-based compound or the salt thereof in step 2) is used in an amount from 0.01 mol % to 10 mol %, preferably 0.05 mol % to 5 mol % of the compound IV;

preferably, step 1) and step 2) are each independently carried out at an reaction temperature from −10 to 150° C., preferably −5 to 120° C., more preferably 0 to 100° C.;

preferably, step 1) and step 2) are each independently carried out for a reaction time from 1 to 24 h, preferably 3 to 18 h;

preferably, step 1) and 2) are carried out in the presence of an organic solvent and an acid-binding agent;

wherein the acid-binding agent is an inorganic base preferably selected from the group consisting of alkali metal carbonates, alkaline earth metal carbonates, alkali metal bicarbonates and alkaline earth metal bicarbonates, for example, from the group consisting of potassium carbonate, potassium bicarbonate, sodium carbonate and sodium bicarbonate; or the acid-binding agent is an organic base preferably selected from the group consisting of aliphatic amines, aromatic amines, alkali metal salts of alcohols, alkyllithium and mixtures thereof, for example, from the group consisting of triethylamine, tripropylamine, N,N-diisopropylethylamine, 4-dimethylaminopyridine, sodium methoxide, sodium ethoxide, phenyllithium, lithium diisopropylamide and lithium hexamethyldisilazide, and most preferably, potassium carbonate or sodium methoxide;

the solvent is selected from the group consisting of aliphatic hydrocarbons, cycloaliphatic hydrocarbons, aromatic hydrocarbons, halogenated hydrocarbons, esters, ethers, ketones, amides, alcohols and mixtures thereof, and preferably is dimethylformamide (DMF);

wherein the hydrocarbons include petroleum ether, hexane, heptane, cyclohexane, toluene, xylene, chloroform, dichloromethane, dichloroethane, chlorobenzene and trichloroethane; the esters include ethyl acetate, methyl acetate, methyl formate, ethyl formate, isopropyl acetate and trimethyl orthoformate; the ethers include diethyl ether, dimethyl ether, tetrahydrofuran, diisopropyl ether, methyl tert-butyl ether, methyl tert-amyl ether and dioxane; the ketones include acetone, butanone, methyl isobutyl ketone and cyclohexanone; the amides include N,N-dimethylformamide, N,N-dimethylacetamide, N-methylformamide, N-methylpyrrolidone and hexamethylphosphoric triamide; and the alcohols include methanol, ethanol, isopropanol and n-propanol.

The aforementioned method for preparing the compound represented by formula I alternatively comprises:

step 1), reacting compound IV that is 4,6-dichloropyrimidine with compound V that is 3-(methoxymethylene) benzofuran-2(3H)-one under the catalysis of 1-methylimidazole or pentetrazol or a salt thereof, to obtain compound IIIa that is methyl (E)-2-{2-[6-chloropyrimidin-4-yloxy]phenyl}-3-methoxyacrylate;

step 2), optionally isolating the compound IIIa;

step 3), optionally using crude the compound IIIa without isolation;

step 4), reacting the compound IIIa) with the compound represented by formula II under the catalysis by 1-methylimidazole or pentetrazol to obtain the azoxystrobin represented by formula I.

In another aspect, the present disclosure provides a method for preparing azoxystrobin represented by formula I:

I

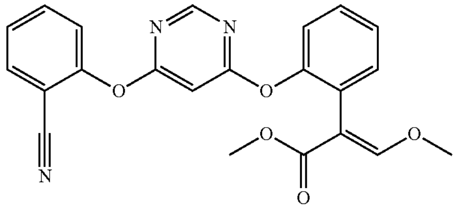

wherein the method comprises:

step 1), reacting compound V with compound VI in the presence of a pentacyclic azole-based compound or a salt thereof to prepare the azoxystrobin represented by formula I, Compound V

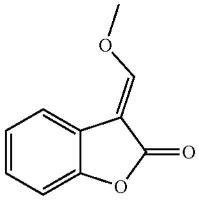

Compound VI

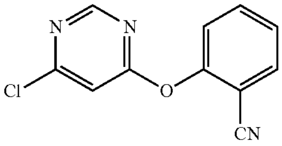

wherein the pentacyclic azole-based compound has a structure selected from the group consisting of:

Formula 1

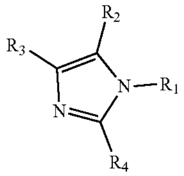

Formula 2

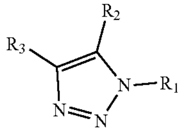

Formula 3

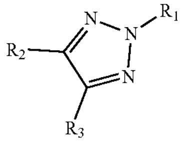

Formula 4

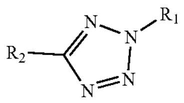

Formula 5

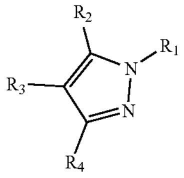

Formula 6

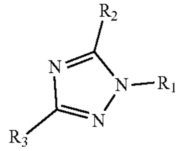

Formula 7

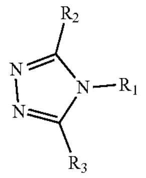

-continued

Formula 8

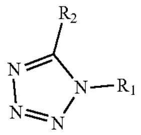

and

Formula 9

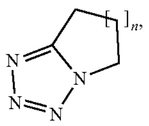

wherein: R1 is selected from the group consisting of C1-C10 straight-chain alkyl, C1-C10 branched-chain alkyl, cyano, amino and C1-C10 alkylamino;

R2-, R3 and R4 are each independently selected from the group consisting of hydrogen, C1-C10 straight-chain alkyl, C1-C10 branched-chain alkyl, cyano, amino, C1-C10 alkylamino, hydroxyl, halogen and nitro;

n is an integer selected from the group consisting of 1, 2 and 3;

preferably, R1 is selected from the group consisting of C1-C6 straight-chain alkyl and C1-C6 branched-chain alkyl; more preferably, R1 is selected from the group consisting of methyl, ethyl, n-propyl, n-butyl, n-pentyl, isopropyl, isobutyl and isopentyl;

preferably, R2-, R3 and R4 are each independently selected from the group consisting of hydrogen, C1-C6 straight-chain alkyl and C1-C6 branched-chain alkyl; more preferably, R2-, R3 and R4 are each independently selected from the group consisting of hydrogen, methyl, ethyl, n-propyl, n-butyl, n-pentyl, isopropyl, isobutyl and isopentyl;

preferably, n is 2 or 3; more preferably, n is 3;

preferably, the pentacyclic azole-based compound is represented by formula 1 or formula 9:

Formula 1

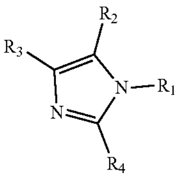

Formula 9

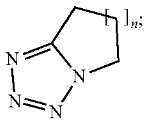

most preferably, the pentacyclic azole-based compound is 1-methylimidazole or pentetrazol.

In another aspect, the method for preparing the compound represented by formula I further comprises:

step 2), preparing the compound VI by reacting a compound represented by formula II with compound IV under the catalysis of the pentacyclic azole-based compound or the salt thereof:

II

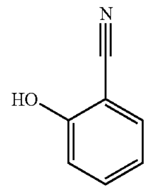

Compound IV

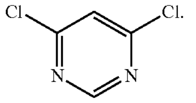

Preferably, the pentacyclic azole-based compound or the salt thereof in step 1) is used in an amount from 0.01 mol % to 10 mol %, preferably 0.05 mol % to 5 mol % of the compound VI; the pentacyclic azole-based compound or the salt thereof in step 2) is used in an amount from 0.01 mol % to 10 mol %, preferably 0.05 mol % to 5 mol % of the compound IV.

Preferably, step 1) and step 2) are each independently carried out at an reaction temperature from −10 to 150° C., preferably −5 to 120° C., more preferably 0 to 100° C.

Preferably, step 1) and step 2) are each independently carried out for a reaction time from 1 to 24 h, preferably 3 to 18 h.

Preferably, step 1) and 2) are carried out in the presence of an organic solvent and an acid-binding agent;

wherein the acid-binding agent is an inorganic base preferably selected from the group consisting of alkali metal carbonates, alkaline earth metal carbonates, alkali metal bicarbonates and alkaline earth metal bicarbonates, for example, from the group consisting of potassium carbonate, potassium bicarbonate, sodium carbonate and sodium bicarbonate; or the acid-binding agent is an organic base preferably selected from the group consisting of aliphatic amines, aromatic amines, alkali metal salts of alcohols, alkyllithium and mixtures thereof, for example, from the group consisting of triethylamine, tripropylamine, N,N-diisopropylethylamine, 4-dimethylaminopyridine, sodium methoxide, sodium ethoxide, phenyllithium, lithium diisopropylamide and lithium hexamethyldisilazide, and most preferably, potassium carbonate or sodium methoxide;

the solvent is selected from the group consisting of aliphatic hydrocarbons, cycloaliphatic hydrocarbons, aromatic hydrocarbons, halogenated hydrocarbons, esters, ethers, ketones, amides, alcohols and mixtures thereof, and preferably is dimethylformamide (DMF); wherein the hydrocarbons include petroleum ether, hexane, heptane, cyclohexane, toluene, xylene, chloroform, dichloromethane, dichloroethane, chlorobenzene and trichloroethane; the esters include ethyl acetate, methyl acetate, methyl formate, ethyl formate, isopropyl acetate and trimethyl orthoformate; the ethers include diethyl ether, dimethyl ether, tetrahydrofuran, diisopropyl ether, methyl tert-butyl ether, methyl tert-amyl ether and dioxane; the ketones include acetone, butanone, methyl isobutyl ketone and cyclohexanone; the amides include N,N-dimethylformamide, N,N-dimethylacetamide, N-methylformamide, N-methylpyrrolidone and hexamethylphosphoric triamide; and the alcohols include methanol, ethanol, isopropanol and n-propanol.

The aforementioned method for preparing the compound represented by formula I alternatively comprises:

step 1), reacting compound IV that is 4,6-dichloropyrimidine with o-cyanophenol represented by formula II under the catalysis by N-methylimidazole or pentylenetetrazole or a salt thereof to obtain the compound VI that is 2-((6-chloropyrimidin-4-yl)oxy)benzonitrile;

step 2), optionally isolating the product of step 1);

step 3), reacting the compound VI that is 2-((6-chloropyrimidin-4-yl)oxy)benzonitrile with the compound V that is 3-(methoxymethylene)benzofuran-2(3H)-one under the catalysis of 1-methylimidazole or pentetrazol or a salt thereof;

step 4), optionally isolating the crude product from the reaction mixture; and step 5), optionally purifying the product to obtain the azoxystrobin.

In another aspect, the present disclosure provides a method for preparing a compound represented by formula III, wherein the method comprises:

reacting compound IV with compound V under the catalysis by a pentacyclic azole-based compound or a salt thereof to obtain a compound represented by formula III:

III

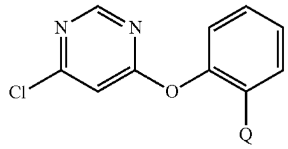

Compound IV

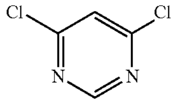

Compound V

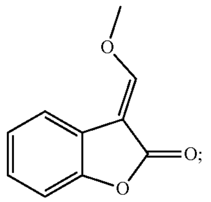

wherein Q is selected from the group consisting of a methyl (E)-2-(3-methoxy)acrylate group ($C(CO_2CH_3)=CHOCH_3$), a methyl 2-(3,3-dimethoxy)propionate group ($C(CO_2CH_3)CH(OCH_3)_2$), and a combination thereof.

Preferably, the pentacyclic azole-based compound or the salt thereof is used in an amount from 0.01 mol % to 10 mol %, preferably 0.05 mol % to 5 mol % of the compound IV.

Preferably, the reaction is carried out at a temperature from −10 to 150° C., preferably −5 to 120° C., more preferably 0 to 100° C.

Preferably, the reaction is carried out for a duration from 1 to 24 h, preferably 3 to 18 h.

Preferably, the reaction is carried out in the presence of an organic solvent and an acid-binding agent.

Preferably, the acid-binding agent is an inorganic base selected from the group consisting of alkali metal carbonates, alkaline earth metal carbonates, alkali metal bicarbonates and alkaline earth metal bicarbonates, for example, from the group consisting of potassium carbonate, potassium bicarbonate, sodium carbonate and sodium bicarbonate; or the acid-binding agent is an organic base preferably selected from the group consisting of aliphatic amines, aromatic amines, alkali metal salts of alcohols, alkyllithium and mixtures thereof, for example, from the group consisting of triethylamine, tripropylamine, N,N-diisopropylethylamine, 4-dimethylaminopyridine, sodium methoxide, sodium ethoxide, phenyllithium, lithium diisopropylamide and lithium hexamethyldisilazide, and most preferably, potassium carbonate or sodium methoxide.

Preferably, the solvent is selected from the group consisting of aliphatic hydrocarbons, cycloaliphatic hydrocarbons, aromatic hydrocarbons, halogenated hydrocarbons, esters, ethers, ketones, amides, alcohols and mixtures thereof, and preferably is dimethylformamide (DMF); wherein the hydrocarbons include petroleum ether, hexane, heptane, cyclohexane, toluene, xylene, chloroform, dichloromethane, dichloroethane, chlorobenzene and trichloroethane; the esters include ethyl acetate, methyl acetate, methyl formate, ethyl formate, isopropyl acetate and trimethyl orthoformate; the ethers include diethyl ether, dimethyl ether, tetrahydrofuran, diisopropyl ether, methyl tert-butyl ether, methyl tert-amyl ether and dioxane; the ketones include acetone, butanone, methyl isobutyl ketone and cyclohexanone; the amides include N,N-dimethylformamide, N,N-dimethylacetamide, N-methylformamide, N-methylpyrrolidone and hexamethylphosphoric triamide; and the alcohols include methanol, ethanol, isopropanol and n-propanol.

In another aspect, the present disclosure provides a method for preparing compound VI, wherein the method comprises:

reacting the compound represented by formula II with compound IV under the catalysis by a pentacyclic azole-based compound or a salt thereof to prepare compound VI:

Compound VI

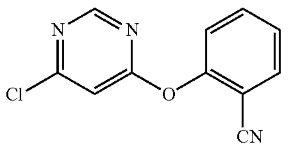

II

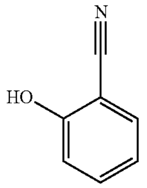

Compound IV

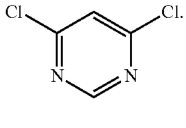

Preferably, the pentacyclic azole-based compound or the salt thereof is used in an amount from 0.01 mol % to 10 mol %, preferably 0.05 mol % to 5 mol % of the compound IV.

Preferably, the reaction is carried out at a temperature from −10 to 150° C., preferably −5 to 120° C., more preferably 0 to 100° C.

Preferably, the reaction is carried out for a duration from 1 to 24 h, preferably 3 to 18 h.

Preferably, the reaction is carried out in the presence of an organic solvent and an acid-binding agent.

Preferably, the acid-binding agent is an inorganic base selected from the group consisting of alkali metal carbonates, alkaline earth metal carbonates, alkali metal bicarbonates and alkaline earth metal bicarbonates, for example, from the group consisting of potassium carbonate, potassium bicarbonate, sodium carbonate and sodium bicarbonate; or preferably the acid-binding agent is an organic base selected from the group consisting of aliphatic amines, aromatic amines, alkali metal salts of alcohols, alkyllithium and mixtures thereof, for example, from the group consisting of triethylamine, tripropylamine, N,N-diisopropylethylamine, 4-dimethylaminopyridine, sodium methoxide, sodium ethoxide, phenyllithium, lithium diisopropylamide and lithium hexamethyldisilazide, and most preferably, potassium carbonate or sodium methoxide.

The solvent is selected from the group consisting of aliphatic hydrocarbons, cycloaliphatic hydrocarbons, aromatic hydrocarbons, halogenated hydrocarbons, esters, ethers, ketones, amides, alcohols and mixtures thereof, and preferably is dimethylformamide (DMF); wherein the hydrocarbons include petroleum ether, hexane, heptane, cyclohexane, toluene, xylene, chloroform, dichloromethane, dichloroethane, chlorobenzene and trichloroethane; the esters include ethyl acetate, methyl acetate, methyl formate, ethyl formate, isopropyl acetate and trimethyl orthoformate; the ethers include diethyl ether, dimethyl ether, tetrahydrofuran, diisopropyl ether, methyl tert-butyl ether, methyl tert-amyl ether and dioxane; the ketones include acetone, butanone, methyl isobutyl ketone and cyclohexanone; the amides include N,N-dimethylformamide, N,N-dimethylacetamide, N-methylformamide, N-methylpyrrolidone and hexamethylphosphoric triamide; and the alcohols include methanol, ethanol, isopropanol and n-propanol.

In another aspect, the aforementioned method for preparing the compound represented by formula I or the intermediate compound represented by formula III, yields the compound represented by formula I or the intermediate represented by formula III with a purity not less than 98%, preferably not less than 99%.

The aforementioned method for preparing the compound represented by formula I yields the product containing an impurity represented by formula VII not higher than 0.3%, preferably not higher than 0.2%, more preferably not higher than 0.1%, most preferably not higher than 0.05%;

VII

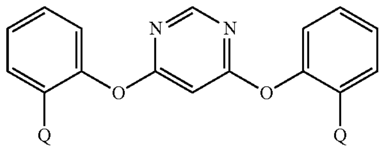

wherein Q is selected from the group consisting of a methyl (E)-2-(3-methoxy)acrylate group ($C(CO_2CH_3)$=$CHOCH_3$), a methyl 2-(3,3-dimethoxy)propionate group ($C(CO_2CH_3)CH(OCH_3)_2$), and a combination thereof.

In accordance with the aforementioned method for preparing the compound represented by formula I, impurities represented by formula VII and formula VIII have a content of not higher than 0.3%, preferably not higher than 0.2%, more preferably not higher than 0.1%, most preferably not higher than 0.05%;

VII

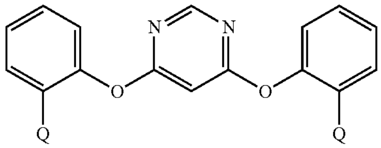

VIII

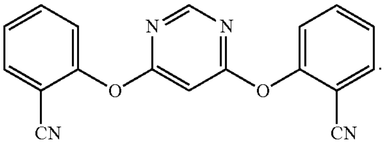

In another aspect, the present disclosure provides a method for controlling a dimer impurity in a product containing azoxystrobin represented by formula I, wherein the dimer impurity has a structure of formula VII and/or formula VIII:

I

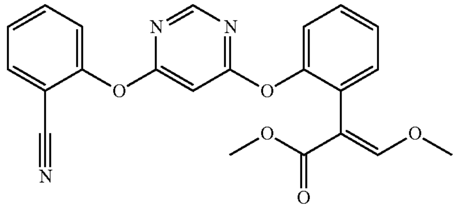

VII

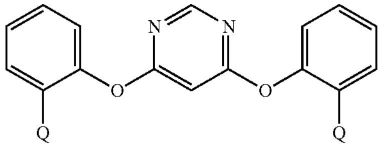

VIII

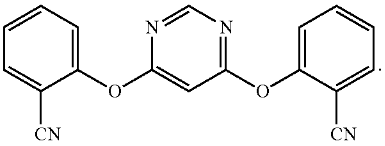

wherein Q is selected from the group consisting of a methyl (E)-2-(3-methoxy)acrylate group ($C(CO_2CH_3)$=$CHOCH_3$), a methyl 2-(3,3-dimethoxy)propionate group ($C(CO_2CH_3)CH(OCH_3)_2$), and a combination thereof;

the product containing azoxystrobin represented by formula I is prepared by:

A) reacting a compound represented by formula II with a compound represented by formula III in the presence of a pentacyclic azole-based compound or a salt, as a catalyst, thereof to prepare the azoxystrobin represented by formula I,

II

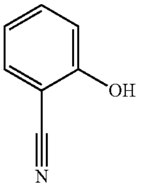

-continued

III

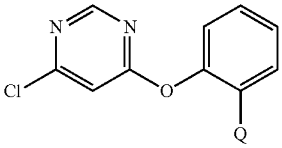

wherein Q is selected from the group consisting of a methyl (E)-2-(3-methoxy)acrylate ($C(CO_2CH_3)$=$CHOCH_3$), a methyl 2-(3,3-dimethoxy)propionate group ($C(CO_2CH_3)CH(OCH_3)_2$), and a combination thereof; or B) reacting compound V with compound VI in the presence of a pentacyclic azole-based compound or a salt, as a catalyst, thereof to prepare the azoxystrobin represented by formula I, Compound V

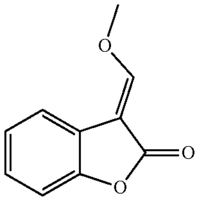

Compound VI

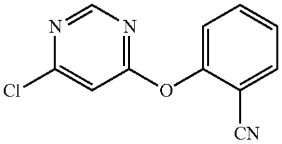

wherein the pentacyclic azole-based compound in the reaction A) and the reaction B) are as defined above.

In the process of preparing the compound of formula III from the compound IV (4,6-dichloropyrimidine) and the compound V (3-(methoxymethylene)benzofuran-2(3H)-one), since the two chlorine atoms on the ring of the raw material 4,6-dichloropyrimidine can both undergo condensation reaction with compound V, higher catalyst activity will result in the more dimer impurity represented by formula VII. Moreover, the dimer impurity is difficult to be removed by conventional purification methods such as recrystallization and slurry, and will remain in the corresponding intermediates and products during the downstream process, which will reduce the purity of the final product azoxystrobin.

Compound III

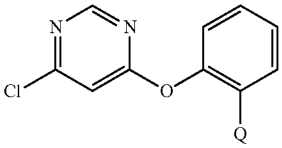

Compound IV

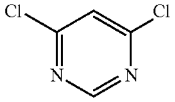

-continued

Compound V

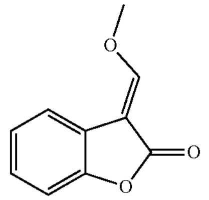

Correspondingly, in the process of preparing compound VI from the compound IV (4,6-dichloropyrimidine) and the compound II (o-cyanophenol), if the two chlorine atoms on the ring of the raw material 4,6-dichloropyrimidine both react with the compound V, then a dimer impurity represented by formula VIII will be generated. Moreover, the dimer impurity is difficult to be removed by conventional purification methods such as recrystallization and slurry, and will remain in the corresponding intermediate and products during the downstream process, which will reduce the purity of the final product azoxystrobin.

In view of the foregoing, a suitable catalyst is desired so as to maintain the products or intermediates at a high purity and minimize the dimer impurities. Although various methods are disclosed in the existing technology for preparing azoxystrobin, none of them focus on how to reduce the dimer impurities existing in the production process. For example, WO2006/114572 and WO2008/043978 disclose use of DABCO as a catalyst, but they do not disclose and/or teach how to reduce dimer impurities.

The method for preparing azoxystrobin and an intermediate thereof using diazabicycloundec-7-ene and diazabicyclnon-5-ene as catalysts, disclosed by WO2020/212919, can reduce dimer impurities, but the catalysts disclosed in this patent document greatly differ, in type, from the catalyst of the present disclosure. Therefore, the catalyst of the present disclosure is not obvious.

The inventors of the present disclosure obtained the pentacyclic azole-based compound of the present disclosure by screening a large numbers of catalysts and through their creative work. The catalyst can be used to prepare azoxystrobin and its intermediate with not only a high yield, but also a high purity, and can greatly reduce the content of dimer impurities in the azoxystrobin product.

Compared with the existing technology, the embodiments according to present disclosure have the beneficial effects of:

(1) Compared with the method for industrially producing azoxystrobin, the method of the present disclosure provides a product with a high purity and can inhibit forming dimer impurities.

(2) The catalyst of the present disclosure is simple in structure, cheap and easy to be prepared, so it can not only reduce the impurity content, but also save cost, as compared with other catalysts disclosed by the existing technology.

(3) The method of the present disclosure is simple, has short process flow, and is easy to be industrialized.

DETAILED DESCRIPTION

The present disclosure is specifically described below in conjunction with examples. It should be noted that the following examples are intended to better illustrate the present disclosure, but not to limit the scope of the present invention. Unless otherwise specified, the materials and reagents used in the following examples are all commercially available.

The following description is made for detailing the present disclosure. It should be understood that unless expressly indicated to the contrary, various alternative modifications and step sequences may be made to the present disclosure. Furthermore, except in any operative example or otherwise indicated, all numbers such as amounts of materials/ingredients used in the specification, are to be understood as modified by the term "about" in all instances.

Therefore, it should be understood that the present invention is not limited to particular illustrated system or process parameters which certainly may vary. It is also to be understood that the terms used herein are for the purpose of describing particular embodiments of the present disclosure and are not intended to limit the scope of the present invention in any way. Examples used anywhere in this specification, including examples of any term discussed herein, are illustrative and not intended to limit the scope and meaning of the present invention or of any exemplified term. Likewise, the present disclosure is not limited to the various embodiments provided in this specification. Unless otherwise defined, all technical and scientific terms used herein have the same meaning as commonly understood by those of ordinary skill in the art to which it pertains. In case of conflict, the present document including definitions shall prevail.

It must be noted that as used in this specification, the singular forms "a", "an" and "the" include plural referents, unless the content expressly dictates otherwise. The terms "preferred" and "preferably" refer to embodiments of the present disclosure that may afford certain benefits under certain circumstances. However, other embodiments may also be preferred under the same or other circumstances. Furthermore, the description of one or more preferred embodiments does not imply that other embodiments are unavailable and is not intended to exclude other embodiments from the scope of the present invention.

As used herein, halogen includes chlorine, bromine, iodine and fluorine.

As used herein, alkali metals include lithium, sodium, potassium, and the like.

As used herein, the terms "comprise", "include", "have", "contain", "involve" and the like are to be construed as open-ended, meaning "include but not limited to".

The salts of the pentacyclic azole-based compounds described herein include: inorganic salts selected from the group consisting of hydrochloride, sulfate, nitrate and phosphate, and organic salts selected from the group consisting of formate, acetate, benzoate, trifluoroacetate, citrate, succinate, maleate, fumarate and oxalate.

The acid-binding agent herein is an inorganic base or an organic base. The inorganic base is selected from the group consisting of metal hydroxides, metal carbonates, and metal bicarbonates. The metal of the inorganic base may be an alkali metal such as lithium, sodium and potassium, or an alkaline earth metal such as magnesium, calcium, strontium and barium. Preferably, the inorganic base is selected from the group consisting of carbonates and bicarbonates, such as potassium carbonate, potassium bicarbonate, sodium carbonate and sodium bicarbonate. The organic base includes, but is not limited to, aliphatic amine, aromatic amine, alkali metal salt of alcohol or alkyl lithium, such as triethylamine, tripropylamine, N,N-diisopropylethylamine, 4-dimethylaminopyridine, sodium methoxide, sodium ethoxide, phenyllithium, lithium diisopropylamide and lithium hexamethyldisilazide. Most preferably, the acid-binding agent is selected from the group consisting of potassium carbonate and sodium methoxide.

The solvent is selected from the group consisting of: aliphatic hydrocarbons, cycloaliphatic hydrocarbons and aromatic hydrocarbons, such as petroleum ether, hexane, heptane, cyclohexane, toluene and xylene; halogenated hydrocarbons such as chloroform, dichloromethane, dichloroethane, chlorobenzene and trichloroethane; esters such as ethyl acetate, methyl acetate, methyl formate, ethyl formate, isopropyl acetate and trimethyl orthoformate; ethers such as diethyl ether, dimethyl ether, tetrahydrofuran, diisopropyl ether, methyl tert-butyl ether, methyl tert-amyl ether and dioxane; ketones such as acetone, butanone, methyl isobutyl ketone and cyclohexanone; amides such as N,N-dimethylformamide, N,N-dimethylacetamide, N-methylformamide, N-methylpyrrolidone and hexamethylphosphoric triamide; alcohols such as methanol, ethanol, isopropanol and n-propanol; and a mixture thereof. In a preferred embodiment, the reaction of the present disclosure is carried out in dimethylformamide (DMF).

Advantages and other parameters of the present disclosure are illustrated by the examples provided below. However, the scope of the present disclosure is not limited by these examples in any way. Although the present disclosure has been described by using specific embodiments, it is apparent to those skilled in the art that certain modifications and equivalents are possible and are intended to be included within the scope of the present invention.

EXAMPLE 1

Preparation of Azoxystrobin (Compound 1A) in the Absence of a Catalyst

Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and the mixed solution was heated to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer,, and the residue in the kettle was crystallized with a mixed solution of methanol and water to obtain the target product with a purity of 87.3%, a dimer content of 0.3% and a yield of 82.4%.

EXAMPLE 2

Preparation of Azoxystrobin (Compound 1A) Using 1 Mol % of 1-Methylimidazole as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with 1-methylimidazole (0.1 g, 99%, 0.0012 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer, and the residue in the kettle was crystallized with a mixed solution of methanol and water, to obtain the target product with a purity of 99.3%, a dimer content of 0.02% and a yield of 95.1%.

EXAMPLE 3

Preparation of Azoxystrobin (Compound 1A) Using 2 Mol % of 1-Methylimidazole as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with N-methylimidazole (0.2 g, 99%, 0.0024 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer,, and the residue in the kettle was crystallized with a mixed solution of methanol and water, to obtain the target product with a purity of 99.6%, a dimer content of 0.03% and a yield of 95.5%.

EXAMPLE 4

Preparation of Azoxystrobin (Compound 1A) Using 10 Mol % of 1-Methylimidazole as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with N-methylimidazole (1 g, 99%, 0.012 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer, and the residue in the kettle was crystallized with a mixed solution of methanol and water to obtain the target product with a purity of 99.3%, a dimer content of 0.05% and a yield of 94.8%.

EXAMPLE 5

Preparation of Azoxystrobin (Compound 1A) Using 1 Mol % of Pentetrazol as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with pentetrazole (0.2 g, 99%, 0.0014 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer, and the residue in the kettle was crystallized with a mixed solution of methanol and water, to obtain the target product with a purity of 99.6%, a dimer content of 0.05% and a yield of 94.9%.

EXAMPLE 6

Preparation of Azoxystrobin (Compound 1A) Using 2 Mol % of Pentetrazol as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with pentetrazole (0.4 g, 99%, 0.0028 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer, and the residue in the kettle was crystallized with a mixed solution of methanol and water, to obtain the target product with a purity of 99.4%, a dimer content of 0.04% and a yield of 95.1%.

EXAMPLE 7

Preparation of Azoxystrobin (Compound 1A) Using 10 Mol % of Pentetrazol as a Catalyst Methyl (E)-2-{2-[6-chloropyrimidin-4-yloxy]phenyl}-3-methoxyacrylate (41.9 g, 96. %, 0.125 mol), 2-cyanophenol (17.8 g, 99%, 0.148 mol) and potassium carbonate (10 g, 98%, 0.071 mol) were mixed in DMF under stirring, and added with pentetrazole (1.8 g, 99%, 0.013 mol). The mixed solution was heated up to 90° C. and kept at 90° C. for 9-10 h. DMF was removed by vacuum distillation. Toluene (100 mL) and water (60 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer, and the residue in the kettle was crystallized with a mixed solution of methanol and water, to obtain the target product with a purity of 99.5%, a dimer content of 0.03% and a yield of 94.9%.

EXAMPLE 8

Preparation of methyl(E)-2-(2-((6-chloropyrimidin-4-yl)oxy)phenyl)-3-methoxyacrylate (Compound IIIa) in the Absence of a Catalyst Solid (Z)-3-(methoxymethylene)benzofuran-2(3H)-one (50 g, 99%, 0.284 mol) and 4,6-dichloropyrimidine (54.97 g, 99%, 0.369 mol) were stirred evenly in toluene to obtain a mixed solution. The mixed solution was adjusted to a temperature of 20-25° C., and slowly dropwise added with sodium methoxide/methanol solution (73.99 g, 29%, 0.397 mol). After the dropwise addition was completed, the mixed solution was kept at this temperature for 1 hour, and added with 100 g of 5% hydrochloric acid. The mixed solution of the two was heated up to 65-70° C., stirred for 30 min, and stood for phase separation. The toluene was recovered by distillation under vacuum at 50-60° C. from the up-layer. The oily residue in the bottle was heated up to 130° C. to 135° C., and added with potassium bisulfate (0.386 g, 0.003 mol). The reaction mixture was stirred at 130° C. to 135° C. under vacuum of 15 mmHg to 22 mmHg for 3 h, and then crystallized with methanol (50 ml) to obtain the target product with a purity of 88.2%, a dimer content of 0.1% and a yield of 82.3%.

EXAMPLE 9

Preparation of methyl(E)-2-(2-((6-chloropyrimidin-4-yl)oxy)phenyl)-3-methoxyacrylate (compound IIIa) Using 2.5 Mol % of 1-Methylimidazole as a Catalyst Solid (Z)-3-(methoxymethylene)benzofuran-2(3H)-one (50 g, 99%, 0.284 mol), 4,6-dichloropyrimidine (54.97 g, 99%, 0.369 mol) and 1-methylimidazole (0.58 g, 99%, 0.007 mol) were stirred evenly in toluene to obtain a mixed solution. The mixed solution was adjusted to a temperature of 20-25° C., and slowly dropwise added with sodium methoxide/methanol solution (73.99 g, 29%, 0.397 mol). After the dropwise addition was completed, the mixed solution was kept at this temperature for 1 hour, and added with 100 g of 5% hydrochloric acid. The mixed solution of the two was heated up to 65-70° C., stirred for 30 min, and stood for phase separation. The toluene was recovered by distillation under vacuum at 50-60° C. from the up-layer. The oily residue in the bottle was heated up to 130° C. to 135° C., and added with potassium bisulfate (0.386 g, 0.003 mol). The reaction mixture was stirred at 130° C. to 135° C. under vacuum of 15 mmHg to 22 mmHg for 3 h, and then crystallized in methanol (50 ml), to obtain the target product with a purity of 97.6%, a dimer content of 0.06% and a yield of 90.2%.

EXAMPLE 10

Preparation of methyl(E)-2-(2-((6-chloropyrimidin-4-yl)oxy)phenyl)-3-methoxyacrylate (Compound IIIa) Using 5 Mol % of 1-Methylimidazole as a Catalyst Solid (Z)-3-(methoxymethylene)benzofuran-2(3H)-one (50 g, 99%, 0.284 mol), 4,6-dichloropyrimidine (54.97 g, 99%, 0.369 mol) and 1-methylimidazole (1.16 g, 99%, 0.014 mol) were stirred evenly in toluene to obtain a mixed solution. The mixed solution was adjusted to a temperature of 20-25° C., and slowly dropwise added with sodium methoxide/methanol solution (73.99 g, 29%, 0.397 mol). After the dropwise addition was completed, the mixed solution was kept at this temperature for 1 hour, and added with 100 g of 5% hydrochloric acid. The mixed solution of the two was heated up to 65-70° C., stirred for 30 min, and stood for phase separation. The toluene was recovered by distillation under vacuum at 50-60° C. from the up-layer. The oily residue in the bottle was heated up to 130° C. to 135° C., and added with potassium bisulfate (0.386 g, 0.003 mol). The reaction mixture was stirred at 130° C. to 135° C. under vacuum of 15 mmHg to 22 mmHg for 3 h, and then crystallized with methanol (50 ml) to obtain the target product with a purity of 98.1%, a dimer content of 0.05% and a yield of 90.8%.

EXAMPLE 11

Preparation of methyl(E)-2-(2-((6-chloropyrimidin-4-yl)oxy)phenyl)-3-methoxyacrylate (Compound IIIa) using 2.5 Mol % of 4-methyl-1,2,4-triazole as a Catalyst Solid (Z)-3-(methoxymethylene)benzofuran-2(3H)-one (50 g, 99%, 0.284 mol), 4,6-dichloropyrimidine (54.97 g, 99%, 0.369 mol) and 4-methyl-1,2,4-triazole (0.59 g, 99%, 0.007 mol) were stirred evenly in toluene to obtain a mixed solution. The mixed solution was adjusted to a temperature of 20-25° C., and slowly dropwise added with sodium methoxide/methanol solution (73.99 g, 29%, 0.397 mol). After the dropwise addition was completed, the mixed solution was kept at this temperature for 1 hour, and added with 100 g of 5% hydrochloric acid. The mixed solution of the two was heated up to 65-70° C., stirred for 30 min, and stood for separation. The solvent in the toluene phase was recovered under vacuum at 50-60° C. The oily residue in the bottle was heated up to 130° C. to 135° C., and added with potassium bisulfate (0.386 g, 0.003 mol). The reaction mixture was stirred at 130° C. to 135° C. under vacuum of 15 mmHg to 22 mmHg for 3 h, and then crystallized with methanol (50 ml) to obtain the target product with a purity of 94.2%, a dimer content of 0.13% and a yield of 85.4%.

EXAMPLE 12

Preparation of methyl(E)-2-(2-((6-chloropyrimidin-4-yl) oxy)phenyl)-3-methoxyacrylate (Compound IIIa) Using 2.5 Mol % of Pentetrazol as a Catalyst Solid (Z)-3-(methoxymethylene)benzofuran-2(3H)-one (50 g, 99%, 0.284 mol), 4,6-dichloropyrimidine (54.97 g, 99%, 0.369 mol) and pentetrazole (0.96 g, 99%, 0.007 mol) were stirred evenly in toluene to obtain a mixed solution. The mixed solution was adjusted to a temperature of 20-25° C., and slowly dropwise added with sodium methoxide/methanol solution (73.99 g, 29%, 0.397 mol). After the dropwise addition was completed, the mixed solution was kept at this temperature for 1 hour, and added with 100 g of 5% hydrochloric acid. The mixed solution of the two was heated up to 65-70° C., stirred for 30 min, and stood for phase separation. The toluene was recovered by distillation under vacuum at 50-60° C. from the up-layer. The oily residue in the bottle was heated up to 130° C. to 135° C., and added with potassium bisulfate (0.386 g, 0.003 mol). The reaction mixture was stirred at 130° C. to 135° C. under vacuum of 15 mmHg to 22 mmHg for 3 h, and then crystallized with methanol (50 ml) to obtain the target product with a purity of 98.6%, a dimer content of 0.04% and a yield of 89.9%.

EXAMPLE 13

Preparation of 2-[(6-chloro-4-pyrimidinyl)oxy]-benzonitrile (Compound VI) Using 2.5 Mol % of 1-Methylimidazole as a Catalyst 4,6-dichloropyrimidine (98%, 92 g, 0.605 mol), potassium carbonate (104.5 g, 0.765 mol) and 1-methylimidazole (1.24 g, 0.015 mol) were mixed in toluene under stirring. The mixture was adjusted to a temperature of 60° C., dropwise added with a solution of o-cyanophenol in toluene, stirred at 60° C. for 6 hours, and then cooled. The organic phase was separated and washed with 5% NaOH, and the aqueous phase was extracted with toluene. The combined organic extract was distilled to remove part of the solvent to obtain a product. The product was crystallized and filtered at 0-5° C., and dried to pure obtain 2-[(6-chloro-4-pyrimidinyl) oxy]-benzonitrile with a purity of 96.5%, a dimer content of 0.17%, and a yield of 94.2%.

EXAMPLE 14

Preparation of Azoxystrobin (Compound 1A) Using 2.5 Mol % of 1-Methylimidazole as a Catalyst A mixture of 3-(methoxymethylene)-2(3H)-benzofuranone (97%, 181.4 g, 1.0 mol) in DMF under stirring was added with 2-[(6-chloro-4-pyrimidinyl)oxy]-benzonitrile (96.6%, 251.6 g, 1.05 mol) at 10° C. to 15° C. The reaction mixture was added with a catalytic amount of 1-methylimidazole (2.06 g, 0.025 mol), and dropwise added with sodium methoxide (30% sodium methoxide/methanol solution, 219 g, 1.22 mol) at 10° C. to 15° C. The reaction material was kept at 10° C. to 15° C. for 1 hour. DMF was removed by vacuum distillation. Toluene (200 mL) and water (120 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer. The oily residue in the bottle was heated up to 130° C. to 135° C., and added with potassium bisulfate (0.127 g, 0.01 mol). The reaction mixture was stirred at 130° C. to 135° C. under vacuum of 15 mmHg to 22 mmHg for 3 h, and then crystallized with methanol (50 ml) to obtain the target product with a purity of 99.2%, a dimer content of 0.03% and a yield of 94.6%.

EXAMPLE 15

Preparation of 2-[(6-chloro-4-pyrimidinyl)oxy]-benzonitrile (Compound VI) Using 2.5 Mol % of Pentetrazol as a Catalyst 4,6-dichloropyrimidine (98%, 92 g, 0.605 mol), potassium carbonate (104.5 g, 0.765 mol) and pentetrazole (2.34 g, 0.015 mol) were mixed in toluene under stirring. The mixture was adjusted to a temperature of 60° C., dropwise added with a solution of o-cyanophenol in toluene, stirred at 60° C. for 6 hours, and then cooled. The organic phase was separated and washed with 5% NaOH, and the aqueous phase was extracted with toluene. The combined organic extract was distilled to remove part of the solvent to obtain a product. The product was crystallized and filtered at 0-5° C., and dried to obtain pure 2-[(6-chloro-4-pyrimidinyl) oxy]-benzonitrile with a purity of 98.8%, a dimer content of 0.05%, and a yield of 94.1%.

EXAMPLE 16

Preparation of Azoxystrobin (Compound 1A) Using 2.5 Mol % of Pentetrazol as a Catalyst A mixture of 3-(methoxymethylene)-2(3H)-benzofuranone (97%, 181.4 g, 1.0 mol) in DMF under stirring was added with 2- [(6-chloro-4-pyrimidinyl) oxy]-benzonitrile (96.6%, 251.6 g, 1.05 mol) at 10° C. to 15° C. The reaction mixture was added with a catalytic amount of pentetrazole (3.4 g, 0.025 mol), and dropwise added with sodium methoxide (30% sodium methoxide/methanol solution, 219 g, 1.22 mol) at 10° C. to 15° C. The reaction material was kept at 10° C. to 15° C. for 1 hour. DMF was removed by vacuum distillation. Toluene (200 mL) and water (120 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer. The oily residue in the bottle was heated up to 130° C. to 135° C., and added with potassium bisulfate (0.127 g, 0.01 mol). The reaction mixture was stirred at 130° C. to 135° C. under vacuum of 15 mmHg to 22 mmHg for 3 h, and then crystallized with methanol (50 ml) to obtain the target product with a purity of 99.1%, a dimer content of 0.07% and a yield of 94.8%.

EXAMPLE 17

Preparation of 2-[(6-chloro-4-pyrimidinyl)oxy]-benzonitrile (Compound VI) in the Absence of a Catalyst 4,6-dichloropyrimidine (98%, 92 g, 0.605 mol) and potassium carbonate (104.5 g, 0.765 mol) were mixed in toluene under stirring. The mixture was adjusted to a temperature of 60° C., dropwise added with a solution of o-cyanophenol in toluene, stirred at 60° C. for 6 hours, and then cooled. The organic phase was separated and washed with 5% NaOH, and the aqueous phase was extracted with toluene. The combined organic extract was distilled to remove part of the solvent to obtain a product. The product was crystallized and filtered at 0-5° C., and dried to obtain pure 2-[(6-chloro-4-pyrimidinyl)oxy]-benzonitrile with a purity of 89.7%, a dimer content of 0.16%, and a yield of 85%.

EXAMPLE 18

Preparation of Azoxystrobin (Compound 1A) in the Absence of a Catalyst

A mixture of 3-(methoxymethylene)-2(3H)-benzofuranone (97%, 181.4 g, 1.0 mol) in DMF under stirring was added with 2- [(6-chloro-4-pyrimidinyl) oxy]-benzonitrile (96.6%, 251.6 g, 1.05 mol) at 10° C. to 15° C. The reaction mixture was dropwise added with sodium methoxide (30% sodium methoxide/methanol solution, 219 g, 1.22 mol) at 10° C. to 15° C. The reaction material was kept at 10° C. to 15° C. for 1 hour. DMF was removed by vacuum distillation. Toluene (200 mL) and water (120 mL) were added to the residue in the distillation kettle, and the mixed solution of toluene and water was heated to 60° C., stirred for 30 min, and then stood for phase separation. The toluene was recovered by distillation under vacuum at 50-60° C. from the up-layer. The oily residue in the bottle was heated up to 130° C. to 135° C., and added with potassium bisulfate (0.127 g, 0.01 mol). The reaction mixture was stirred at 130° C. to 135° C. under vacuum of 15 mmHg to 22 mmHg for 3 h, and then crystallized with methanol (50 ml) to obtain the target product with a purity of 83.4%, a dimer content of 0.13% and a yield of 83.2%.

The invention claimed is:

1. A method for preparing azoxystrobin represented by formula I,

I

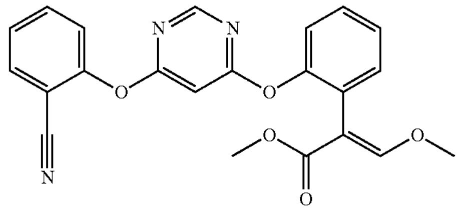

the method comprising step 1), reacting a compound represented by formula II with a compound represented by formula III in the presence of an azole-based compound or the salt thereof as an only catalyst to prepare the azoxystrobin represented by formula I,

II

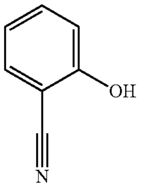

-continued

III

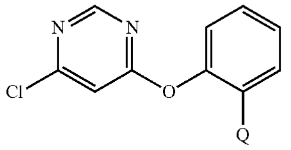

wherein Q is selected from the group consisting of a methyl (E)-2-(3-methoxy) acrylate group, a methyl 2-(3,3-dimethoxy) propionate group, and a combination thereof;

wherein the azole-based compound is represented by formula 1 or formula 9:

Formula 1

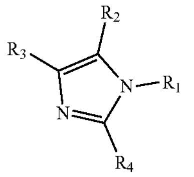

Formula 9

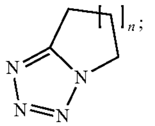

$R_1$ is selected from the group consisting of $C_1$-$C_{10}$ straight-chain alkyl, $C_1$-$C_{10}$ branched-chain alkyl, cyano, amino and $C_1$-$C_{10}$ alkylamino;

$R_2$, $R_3$ and $R_4$ are each independently selected from the group consisting of hydrogen, $C_1$-$C_{10}$ straight-chain alkyl, $C_1$-$C_{10}$ branched-chain alkyl, cyano, amino, $C_1$-$C_{10}$ alkylamino, hydroxyl, halogen and nitro;

n is an integer selected from the group consisting of 1, 2 and 3.

2. The method according to claim 1, further comprising:

step 2), reacting compound IV with compound V under the catalysis by the azole-based compound or the salt thereof to prepare the compound represented by formula III:

Compound IV

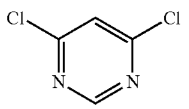

Compound V

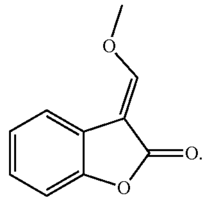

3. The method according to claim 2, wherein:

the azole-based compound or the salt thereof in step 1) is used in an amount from 0.01 mol % to 10 mol % of the compound represented by formula III; the azole- based compound or the salt thereof in step 2) is used in an amount from 0.01 mol % to 10 mol % of the compound IV.

4. The method for preparing the azoxystrobin represented by formula I according to claim 1, which yields the azoxystrobin represented by formula I with a purity of not less than 98% by mass.

5. The method for preparing the azoxystrobin represented by formula I according to claim 2, which yields the product containing an impurity represented by formula VII not higher than 0.3%,

VII

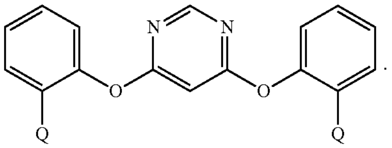

wherein Q is selected from the group consisting of a methyl (E)-2-(3-methoxy) acrylate group, a methyl 2-(3,3-dimethoxy) propionate group, and a combination thereof.

6. The method according to claim 1, wherein $R_1$ is selected from the group consisting of $C_1$-$C_6$ straight-chain alkyl and $C_1$-$C_6$ branched-chain alkyl;

$R_2$, $R_3$ and $R_4$ are each independently selected from the group consisting of hydrogen, $C_1$-$C_6$ straight-chain alkyl and $C_1$-$C_6$ branched-chain alkyl; and n is 2 or 3.

7. The method according to claim 6, wherein $R_1$ is selected from the group consisting of methyl, ethyl, n-propyl, n-butyl, n-pentyl, isopropyl, isobutyl and isopentyl;

$R_2$, $R_3$ and $R_4$ are each independently selected from the group consisting of hydrogen, methyl, ethyl, n-propyl, n-butyl, n-pentyl, isopropyl, isobutyl and isopentyl; and n is 3.

8. The method according to claim 1, wherein the azole-based compound is 1-methylimidazole or pentetrazol.

9. The method according to claim 2, wherein:

step 1) and step 2) are each independently carried out at a reaction temperature from −10 to 150° C. for a reaction time from 1 to 24 h in the presence of an organic solvent and an acid-binding agent, wherein the acid-binding agent is selected from the group consisting of alkali metal carbonates, alkaline earth metal carbonates, alkali metal bicarbonates, alkaline earth metal bicarbonates, aliphatic amines, aromatic amines, alkali metal salts of alcohols, and alkyllithium, the organic solvent is selected from the group consisting of aliphatic hydrocarbons, cycloaliphatic hydrocarbons, aromatic hydrocarbons, halogenated hydrocarbons, esters, ethers, ketones, amides, alcohols and mixtures thereof.

10. The method according to claim 9, wherein:

the acid-binding agent is selected from the group consisting of potassium carbonate, potassium bicarbonate, sodium carbonate, sodium bicarbonate, triethylamine, tripropylamine, N,N-diisopropylethylamine, 4-dimethylaminopyridine, sodium methoxide, sodium ethoxide, phenyllithium, lithium diisopropylamide and lithium hexamethyldisilazide;

the organic solvent is selected from the group consisting of petroleum ether, hexane, heptane, cyclohexane, toluene, xylene, chloroform, dichloromethane, dichloroethane, chlorobenzene and trichloroethane, ethyl acetate, methyl acetate, methyl formate, ethyl formate, isopropyl acetate, trimethyl orthoformate, diethyl ether, dimethyl ether, tetrahydrofuran, diisopropyl ether, methyl tert-butyl ether, methyl tert-amyl ether, dioxane, acetone, butanone, methyl isobutyl ketone, cyclohexanone, N,N-dimethylformamide, N,N-dimethylacetamide, N-methylformamide, N-methylpyrrolidone, hexamethylphosphoric triamide, methanol, ethanol, isopropanol and n-propanol.

* * * * *